(12) United States Patent
Kudo et al.

(10) Patent No.: US 8,153,769 B2
(45) Date of Patent: Apr. 10, 2012

(54) PROCESS FOR PRODUCING PROTEOGLYCAN

(75) Inventors: Yoshiaki Kudo, Hokkaido (JP); Masaki Narumi, Hokkaido (JP)

(73) Assignees: Kushiro Industrial Technology Center, Hokkaido (JP); Yoshiaki Kudo, Hokkaido (JP); Biomatec Japan, Inc., Hokkaido (JP)

( * ) Notice: Subject to any disclaimer, the term of this patent is extended or adjusted under 35 U.S.C. 154(b) by 431 days.

(21) Appl. No.: 12/224,013

(22) PCT Filed: Feb. 9, 2007

(86) PCT No.: PCT/JP2007/052317
§ 371 (c)(1),
(2), (4) Date: Aug. 14, 2008

(87) PCT Pub. No.: WO2007/094248
PCT Pub. Date: Aug. 23, 2007

(65) Prior Publication Data
US 2010/0234580 A1 Sep. 16, 2010

(30) Foreign Application Priority Data
Feb. 14, 2006 (JP) .................. 2006-036277

(51) Int. Cl.
*C07K 1/00* (2006.01)
(52) U.S. Cl. ........................ 530/395; 530/412
(58) Field of Classification Search .......... None
See application file for complete search history.

(56) References Cited

U.S. PATENT DOCUMENTS

| 4,297,272 A | 10/1981 | D-Hinterland et al. |
| 4,397,838 A | 8/1983 | d-Hinterland et al. |
| 6,803,454 B2 | 10/2004 | Takagaki |
| 2007/0010430 A1 | 1/2007 | Sato et al. |

FOREIGN PATENT DOCUMENTS

| EP | 0 013 851 | 8/1980 |
| JP | 4-220401 | 8/1992 |
| JP | 2001-172296 A | 6/2001 |
| JP | 2002-069097 A | 3/2002 |
| JP | 2003-268004 | 9/2003 |
| JP | 2009-173702 A | 8/2009 |
| WO | 2004/083257 A1 | 9/2004 |

OTHER PUBLICATIONS

English translation of: Nishikiori et al., Hoakkaido Kushiro Fisheries Experimental Station Jigyo Hokokusho, 99: 128-129 (2000).*
Nishikiori et al., Hokkaido Kushiro Fisheries Experimental Station Jigyo Hokokusho, 99:128-129 (2000).

* cited by examiner

*Primary Examiner* — Suzanne M Noakes
(74) *Attorney, Agent, or Firm* — Peter F. Corless; Christine C. O'Day; Edwards Wildman Palmer LLP

(57) ABSTRACT

An efficient low-cost method of proteoglycan recovery from natural resources. There is provided a process for producing proteoglycan, comprising the steps of immersing a biological sample containing proteoglycan in an alkali solution of 0.0025 to 0.1 N and recovering the solution after the immersion. As compared with the conventional extraction method, proteoglycan can be recovered in unaltered undecomposed form easily within a short period of time, thereby attaining substantial reduction of proteoglycan production cost. Further, proteoglycan highly useful in industry can be recovered from wasted portions of fin, feather, mammal, etc. having mainly been discarded, thereby contributing toward effective utilization of industrial waste and reduction of the volume of industrial waste per se.

6 Claims, 1 Drawing Sheet

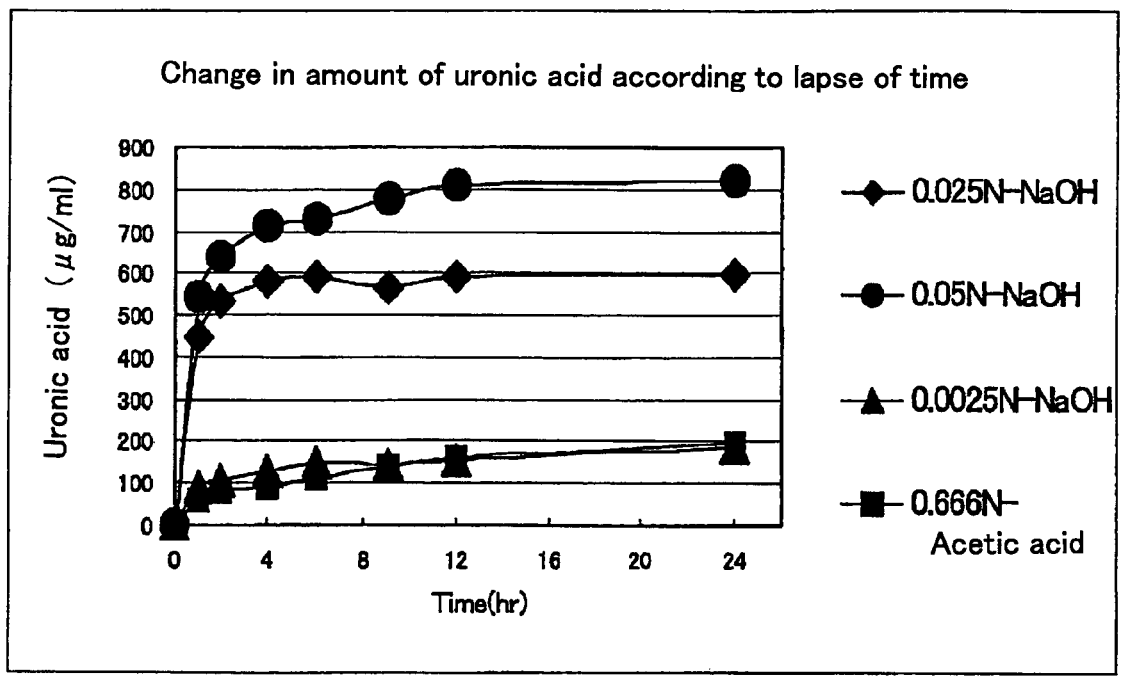

PROCESS FOR PRODUCING PROTEOGLYCAN

TECHNICAL FIELD

The present invention relates to a process for producing proteoglycan, which is useful as a material for preparing pharmaceuticals, medical supplies, cosmetics, food products, and industrial products, etc., including the steps of extracting it from a biological sample containing proteoglycan, for example, a cartilage tissue of a fish, a mollusk, a bird and a mammal and producing it therefrom.

Proteoglycan is a general name which refers to a glycoprotein with very complex and multiple types of structures and it generally consists of a single core protein with several to several tens of linear sugar chains covalently linked. The most typical sugar chain that is included in proteoglycan found in cartilage tissue is chondroitin sulfate.

Chondroitin sulfate is a component which draws attention in the industry in view of high usefulness such as having good moisturizing property, biocompatibility or lubricant property, chondroitin sulfate, and many processes for its efficient recovery and preparation from natural resources are developed.

In cartilage tissues, chondroitin sulfate is not present alone by itself. Rather, it is present in a complex form with a protein, i.e., in a form of proteoglycan. In this regard, extraction of proteoglycan without any change is often difficult due to a complicated structure of glycoprotein complex. For such reason, a process of extracting chondroitin sulfate only, after completely degrading the portion of a core protein of proteoglycan, has been typically employed. The product of such process is a mucopolysaccharide such as chondroitin sulfate, etc.

Meanwhile, there has been also an effort to recover, prepare and use the proteoglycan itself instead of chondroitin sulfate. Especially in cartilage tissues of a fish, a bird and a mammal, proteoglycan having chondroitin sulfate as a main sugar chain is included. Moreover, in view of the fact that such cartilage tissues have been generally discarded as a waste, several processes of producing proteoglycan from cartilage tissues were proposed, also as an effective way of utilizing waste.

For instances, there has been reported methods that proteoglycan is extracted from nasal cartilage of salmon by using guanidinium hydrochloride (Patent Document 1) and by using acetic acid (Patent Document 2). However, unfortunately it can not be said that conventional methods like them are at the level of commercial application since cost involved for extraction and purification is quite high.

Patent Document 1 Japanese Patent Application Laid-Open No. 2001-172296
Patent Document 2: JP-A No. 2002-69097

DISCLOSURE OF THE INVENTION

Problem to be Solved by the Invention

An object of the present invention is to develop a low-cost process for producing orally ingestible proteoglycan from a fish, a mollusk, a bird or a mammal, especially from their wasted portions.

Means for Solving the Problems

Inventors of the present invention found that by using an alkali solution, that has been regarded inappropriate for recovery and preparation of protein and protein complex, under a certain condition, proteoglycan which is a glycoprotein complex can be efficiently recovered from a cartilage tissue and other biological sample containing proteoglycan, and therefore completed each of the invention described below.

(1) A process for producing proteoglycan including the steps of immersing a biological sample containing proteoglycan in an alkali solution of 0.0025 to 0.1 N and recovering the solution after the immersion.

(2) The process described in above (1), which further includes a step of separating proteoglycan from the recovered solution.

(3) The process described in above (1) or (2), in which the alkali solution is a solution of alkali metal salt.

(4) The process described in any one of above (1) to (3), in which the biological sample containing proteoglycan is a cartilage tissue, muscular fibrils or leather of a fish, a mollusk, a bird or a mammal.

(5) The process described in above (4), in which the biological sample containing proteoglycan is a cartilage tissue of a fish, a bird or a mammal.

Effect of the Invention

As compared with the conventional extraction method, according to the process of the present invention, proteoglycan can be easily recovered in unaltered and undecomposed form within a short period of time, thereby attaining substantial reduction of proteoglycan production cost. Further, proteoglycan highly useful in industry can be recovered from wasted portions of a fish, a bird or a mammal having mainly been discarded, thereby contributing toward effective utilization of industrial waste and reduction of the volume of industrial waste itself.

Moreover, in the present invention, a proteolytic enzyme inhibitor to inactivate a proteolytic enzyme that is included in biological tissues is not necessarily to be added. Since such inhibitor is not always effective for every proteolytic enzyme and many inhibitors by themselves are harmful to human, it is undesirable to use an inhibitor for producing proteoglycan as a material of food product. In this connection, since such inhibitor is not required in the present invention, above problems can be avoided.

BRIEF DESCRIPTION OF THE DRAWINGS

FIG. 1 is a diagram showing an amount of proteoglycan that is recovered by using sodium hydroxide and acetic acid.

BEST MODE FOR CARRYING OUT THE INVENTION

The present invention is directed to a method for extraction and preparation of proteoglycan containing proteins that are generally unstable under heat and in alkali, based on an idea of using an alkali solution, though, which is clearly against the conventional belief.

Proteoglycan is a complex of sugar and a protein. However, since the sugar chain bound to the core protein has a weak bonding, it tends to get easily separated from each other. For such reason, extraction or purification of proteoglycan is extremely difficult per se and a more careful approach is required compared to collagen that consists only of a protein, or chondroitin sulfate that consists only of a carbohydrate.

Thus, conventional processes are not appropriate for a mass production of proteoglycan, due to complicated or manual operation steps, etc.

In addition to the above, proteins are generally unstable under heat, acid, especially alkali, thus easily denatured and degraded. Based on such property of proteins, a method of degrading the proteins by aggressively using an alkali is known. However, it has not been known that proteoglycan, which is a glycoprotein complex, can be extracted with an alkali while the protein portions thereof are protected from degradation.

The process of the present invention can be applied to a biological sample containing proteoglycan such as a cartilage tissue, muscular fibrils or leather of a fish, a mollusk, a bird or a mammal. Preferably, however, it is applied to a cartilage tissue thereof. The cartilage tissue used in the present invention can be those of a fish, a bird or a mammal, especially wasted portions thereof. The cartilage tissue described in the present invention means a cartilage tissue itself, or all other tissues containing a region surrounding the cartilage tissue such as a bone, muscular fibrils, and leather, etc.

According to the present invention, a nasal cartilage tissue of a salmon, which is contained in an average weight of about 6% in salmon head and usually referred to as "hiz", is preferably used. When salmons are caught from the sea near Hokkaido (they are mostly the salmons belonging to Oncorhynchus keta) and processed, their head parts are usually regarded as a waste. Although some of the separated head parts are processed for producing fish powder, they are mostly discarded as an industrial waste. Therefore, "hiz" can be conveniently and stably obtained from such waste at low cost.

According to the present invention, in addition to the hiz described above, a cartilage tissue originating from a fish such as a skate and a shark, etc., a cartilage tissue originating from a bird such as a chicken, and a cartilage tissue originating from a mammal such as a neck or bronchus cartilage of a cow and a cartilage of a whale, etc. can be used. In addition, it has been known that proteoglycan is also found in epidermis of a mollusk such as a squid or an octopus, the outer skin of such mollusk can be also used in the present invention. Especially for the epidermis of a squid, it has been reported that a chondroitin-protein complex which is almost free of any sulfate is found and such chondroitin makes up 70% or more of mucopolysaccharides found in the epidermis of a squid (Suyama et al., "Use of a squid", published November 1980, page 93, Kouseisha). Therefore, outer skins of a squid are useful as one example of a biological sample containing proteoglycan in the present invention. Most of the biological samples containing proteoglycan described above are industrial wastes so that they can be easily obtained. These materials are preferably chopped to a size as small as possible to increase their surface area for better extraction amount of proteoglycan, before their immersion in an alkali solution as described below.

With respect to the alkali solution of the present invention, an aqueous solution such as an aqueous solution of an alkali metal or salts thereof and an aqueous solution of an alkaline earth metal or salts thereof can be appropriately used. However, in terms of efficiency for proteoglycan extraction and convenience for post-treatment, etc., an aqueous solution of an alkali metal, i.e., sodium hydroxide (NaOH), sodium hydrocarbonate, calcium carbonate and potassium hydroxide are preferably used. Most preferably, sodium hydroxide is used.

Concentration of the alkali solution is 0.0025 N to 0.1 N, preferably is 0.01 N to 0.05 N. When an alkali solution of 0.0025 N to 0.01 N is used, it is preferred that the immersion is carried out for at least 9 hours. Further, when an alkali solution of 0.01 N to 0.05 N is used, it is preferred that the immersion is carried out for about 9 hours. Still further, when an alkali solution of 0.05 N to 0.1 N is used, it is preferred that the immersion is carried out for 9 hours or less. Still further, when an alkali solution of 0.01 N to 0.1 N is used, it is preferred that the extraction is carried out for about 2 hours so that the degradation of the core proteins of proteoglycan can be inhibited. According to such treatment conditions, proteoglycan with higher molecular weight can be recovered and prepared.

Immersion of a cartilage tissue in an alkali solution is carried out at the temperature of between 0° C. and room temperature, preferably between 0° C. and 10° C., and more preferably between 0° C. and 4° C. Especially when the immersion temperature is set between 0° C. and 4° C., proteoglycan is hardly degraded so that it can be extracted as a polymeric glycoprotein complex.

The immersion can be carried out by using the alkali solution from 2 to 15 times by weight, preferably 4 to 12 times, more preferably 6 to 12 times by weight compared to the weight of the cartilage tissue. Preferably, the immersion is carried out with stirring by a mixer or a stirrer.

Extraction of proteoglycan from a cartilage tissue can be monitored by detecting and quantifying the amount of uronic acid in accordance with a known method such as Galambos method, (John et al., ANALYTICAL BIOCHEMISTRY, 1967, Vol. 19, page 119-132). However, other known methods can be also used to detect and monitor uronic acid.

In the alkali solution obtained upon the termination of the immersion, a great deal of residuals after the extraction of proteoglycan are contained. As such, they are preferably removed by filtration, centrifugation, or other methods. An extract including proteoglycan can be used as it is as a product. However, it is preferable that it is isolated and purified by an appropriate method to the purity level that is required for various use thereof.

According to the present invention, a special method is not necessarily required for the purification of proteoglycan. However, centrifugation as a preferred method is mentioned. By a process of centrifugation, a fine solid can be conveniently separated as a precipitated residuals, and oily portions from the raw material can be conveniently separated as floating matter on surface.

In addition, a liquid phase containing proteoglycan which is recovered by centrifugation can be further filtered by using a filter paper or a separation apparatus for ultrafilter membrane having an appropriate cut-off molecular weight, etc. For the molecular weight of size exclusion, it can be used as far as the range of from approximately 50,000 Dalton to 1,000,000 Dalton. For such process, if a filter having cut-off molecular weight of 500,000 Dalton or more is used, even a collagen can be removed from a liquid phase so that the purity of proteoglycan can be improved. Further, by lowering the viscosity of the liquid phase by adding water to the liquid phase including proteoglycan, penetration through the membrane can be facilitated. Still further, by repeating this process, a fishy smell that is slightly generated during the process can be also removed.

In addition, by adding thus-obtained concentrate to ethanol that is saturated with sodium chloride, proteoglycan in gel state can be recovered. Such proteoglycan in gel state can be formed into a solid by using a vacuum lyophilizer. Alternatively, it can be dried by using a spray dryer to give a solid in powder form.

Herein below, the present invention is described in more detail with reference to the following examples. However, the present invention is not limited thereto.

EXAMPLES

Example 1

Nasal cartilage removed from a head part of Oncorhynchus keta salmon that had been frozen and stored at −40° C. was chopped using an electric meat chopper into tiny pieces in minced shape. 200.00 g of such minced pieces were used as a starting material. To a 5 liter extraction vessel, 2397.60 g of distilled water that had been previously chilled to 0° C. was added and 2.40 g of solid sodium hydroxide was further added thereto to prepare 2400.00 g in total of an aqueous solution of sodium hydroxide (0.025 N). To this extraction vessel, the above-described starting material (200.00 g) was added and immersed for 9 hours while stirring the contents with a stirrer.

Upon completion of the immersion, the contents were transferred to another vessel over which a stainless steel filter (1 mm) was placed so that an extract including proteoglycan can be recovered.

The extract was subjected to centrifugation for 20 minutes at 3500 rpm by using a centrifuge (IWAKI CFS-400 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using PREP/SCALE TFF membrane (cut-off molecular weight 100,000 Dalton, manufactured by Millipore, Japan), cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 200.00 g of the staring material, 6.64 g of dried solid, which corresponds to 3.32% of the starting material in a conversion value, was obtained.

Furthermore, the amount of amino acid was determined by testing the concentrate using an automatic amino acid analyzer (L-8500 Amino Acid Analyzer, manufactured by Hitachi Ltd.) to quantify the amount of collagen contained in the concentrate. In addition, by following Galambos method, the amount of uronic acid was determined to calculate the amount of proteoglycan.

Still furthermore, by using high speed liquid chromatography (TSK-GEL G4000PWXL column, manufactured by Shimadzu Corporation), the molecular weight of proteoglycan was determined.

As a result of these analyses, it was found that the solid includes 25.0% of protein, 21.5% of ash contents, 52.9% of carbohydrates and 0.6% of lipids. According to the description of Patent Document 1, the weight ratio of the core protein in proteoglycan is about 7.0%. Since the amount of carbohydrates found for the present test was about 52.9%, it is presumed that the proteoglycan of the present invention has purity of about 57%. In addition, it was found that the molecular weight of proteoglycan is about 2,200,000 Dalton.

With respect to the operational processes described for the above example, the concentration of sodium hydroxide was changed to 0.0025 N, 0.025 N or 0.05 N and 0.666 N acetic acid was used instead of sodium hydroxide for the immersion and the extraction for 24 hours. As a result, an observed change in the recovery amount of proteoglycan (i.e., the amount of uronic acid) according to the lapse of time is shown in FIG. 1.

Example 2

Nasal cartilage removed from a head part of Oncorhynchus keta salmon that had been frozen and stored at −40° C. was chopped using an electric meat chopper into tiny pieces in minced shape and immersed in acetone, and the nasal cartilage was dehydrated and defatted. 24.00 g of the treated nasal cartilage, after air drying or drying under reduced pressure, were used as a starting material. To a 5 liter extraction vessel, 2997.75 g of distilled water that had been previously chilled to 5° C. was added and 2.25 g of solid sodium hydroxide was further added thereto to prepare 3000.00 g in total of an aqueous solution of sodium hydroxide (0.02 N). To this extraction vessel, the above-described starting material (24.00 g) was added and immersed for 9 hours while stirring the contents with a stirrer.

Upon completion of the immersion, the contents were transferred to another vessel over which a stainless steel filter (1 mm) was placed so that the nasal cartilage is removed and an extract including proteoglycan can be recovered.

The extract was subjected to centrifugation for 20 minutes at 3000 rpm by using a centrifuge (Hitachi himacCF7D2 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using BIOMAX 100K POLYETHERSULFONE (cut-off molecular weight 100,000 Dalton, manufactured by Millipore, Japan), cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 24.00 g of the staring material, 7.50 g of dried solid, which corresponds to 30.29% of the starting material in a conversion value, was obtained.

Furthermore, the amount of amino acid was determined by testing the concentrate using an automatic amino acid analyzer (L-8500 Amino Acid Analyzer, manufactured by Hitachi Co. Ltd.) to quantify the amount of collagen contained in the concentrate. In addition, by following Galambos method, the amount of uronic acid was determined to calculate the amount of proteoglycan. Still furthermore, by using high speed liquid chromatography (TSK-GEL G4000PWXL column, manufactured by Shimadzu Corporation), the molecular weight of proteoglycan was determined.

As a result of these analyses, it was found that the solid includes 11.8% of protein, 18.4% of ash contents, 67.8% of carbohydrates and 0.0% of lipids. According to the description of Patent Document 1, the weight ratio of the core protein in proteoglycan is about 7.0%. Thus, the presumed purity of the proteoglycan of the present invention was calculated to be 91.1% (i.e., (carbohydrates×0.07+lipids)/(carbohydrates+ proteins+lipids)×100=91.1%). In addition, it was found that the molecular weight of proteoglycan is about 1,200,000 Dalton.

Example 3

Nasal cartilage removed from a head part of Oncorhynchus keta salmon that had been frozen and stored at −40° C. was chopped using an electric meat chopper into tiny pieces in minced shape and immersed in acetone, and the nose cartilage was dehydrated and defatted. 17.90 g of the treated nasal cartilage, after air drying or drying under reduced pressure, were used as a starting material. To a 5 liter extraction vessel, 2322.67 g of distilled water that had been previously chilled to 5° C. was added and 2.33 g of solid potassium hydroxide was further added thereto to prepare 2325 g in total of an aqueous solution of potassium hydroxide (0.018 N). To this extraction vessel, the above-described starting material (17.90 g) was added and immersed for 9 hours while stirring the contents with a stirrer.

Upon completion of the immersion, the contents were transferred to another vessel over which a stainless steel filter (1 mm) was placed so that the nasal cartilage is removed and an extract including proteoglycan can be recovered.

The extract was subjected to centrifugation for 20 minutes at 3000 rpm by using a centrifuge (Hitachi himacCF7D2 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using BIOMAX 100K POLYETHERSULFONE (cut-off molecular weight 100,000 Dalton, manufactured by Millipore, Japan), cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 17.90 g of the staring material, 5.29 g of dried solid, which corresponds to 29.61% of the starting material in a conversion value, was obtained.

Furthermore, the amount of amino acid was determined by testing the concentrate using an automatic amino acid analyzer (L-8500 Amino Acid Analyzer, manufactured by Hitachi Co. Ltd.) to quantify the amount of collagen contained in the concentrate. In addition, by following Galambos method, the amount of uronic acid was determined to calculate the amount of proteoglycan. Still furthermore, by using high speed liquid chromatography (TSK-GEL G4000PWXL column, manufactured by Shimadzu Corporation), the molecular weight of proteoglycan was determined.

As a result of these analyses, it was found that the solid includes 14.0% of protein, 22.4% of ash contents, 63.6% of carbohydrates and 0.0% of lipids. According to the description of Patent Document 1, the weight ratio of the core protein in proteoglycan is about 7.0%. Thus, the presumed purity of the proteoglycan of the present invention was calculated to be 87.7% (i.e., (carbohydrates×0.07+lipids)/(carbohydrates+proteins+lipids)×100=87.7%). In addition, it was found that the molecular weight of proteoglycan is about 1,200,000 Dalton.

Example 4

Cartilage removed from a chicken carina from which flesh had been manually removed was chopped using an electric meat chopper into tiny pieces in minced shape and immersed in acetone, and the cartilage of the chicken carina was dehydrated and defatted. 44.40 g of the treated cartilage, after air drying or drying under reduced pressure, were used as a starting material. To a 5 liter extraction vessel, 2997.75 g of distilled water that had been previously chilled to 5° C. was added and 2.25 g of solid sodium hydroxide was further added thereto to prepare 3000.00 g in total of an aqueous solution of sodium hydroxide (0.02 N). To this extraction vessel, the above-described starting material (44.40 g) was added and immersed for 9 hours while stirring the contents with a stirrer.

Upon completion of the immersion, the contents were transferred to another vessel over which a stainless steel filter (1 mm) was placed so that the cartilage is removed and an extract including proteoglycan can be recovered.

The extract was subjected to centrifugation for 20 minutes at 3000 rpm by using a centrifuge (Hitachi himacCF7D2 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using BIOMAX 100K POLYETHERSULFONE (cut-off molecular weight 100,000 Dalton, manufactured by Millipore, Japan), cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 44.40 g of the staring material, 9.87 g of dried solid, which corresponds to 22.23% of the starting material in a conversion value, was obtained.

Furthermore, the amount of amino acid was determined by testing the concentrate using an automatic amino acid analyzer (L-8500 Amino Acid Analyzer, manufactured by Hitachi Co. Ltd.) to quantify the amount of collagen contained in the concentrate. In addition, by following Galambos method, the amount of uronic acid was determined to calculate the amount of proteoglycan. Still furthermore, by using high speed liquid chromatography (TSK-GEL G4000PWXL column, manufactured by Shimadzu Corporation), the molecular weight of proteoglycan was determined.

As a result of these analyses, it was found that the solid includes 31.3% of protein, 16.9% of ash contents, 51.8% of carbohydrates and 0.0% of lipids. According to the description of Patent Document 1, the weight ratio of the core protein in proteoglycan is about 7.0%. Thus, the presumed purity of the proteoglycan of the present invention was calculated to be 66.7% (i.e., (carbohydrates×0.07+lipids)/(carbohydrates+proteins+lipids)×100=66.7%). In addition, it was found that the molecular weight of proteoglycan is about 920,000 Dalton (16%) and about 460,000 Dalton (84%).

Example 5

Cartilage which had been manually removed from a skater (Dipturus kwangtungensis) was chopped using an electric meat chopper into tiny pieces in minced shape and immersed in acetone, and the cartilage was dehydrated and defatted. 12.00 g of the treated cartilage, after air drying or drying under reduced pressure, were used as a starting material. To a 5 liter extraction vessel, 1678.74 g of distilled water that had been previously chilled to 5° C. was added and 1.26 g of solid sodium hydroxide was further added thereto to prepare 1680.00 g in total of an aqueous solution of sodium hydroxide (0.02 N). To this extraction vessel, the above-described starting material (12.00 g) was added and immersed for 9 hours while stirring the contents with a stirrer.

Upon completion of the immersion, the contents were transferred to another vessel over which a stainless steel filter (1 mm) was placed so that that the cartilage is removed and an extract including proteoglycan can be recovered.

The extract was subjected to centrifugation for 20 minutes at 3000 rpm by using a centrifuge (Hitachi himacCF7D2 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using BIOMAX 100K POLYETHERSULFONE (cut-off molecular weight 100,000 Dalton, manufactured by Millipore, Japan), cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 12.00 g of the staring material, 2.15 g of dried solid, which corresponds to 17.92% of the starting material in a conversion value, was obtained.

Furthermore, the amount of amino acid was determined by testing the concentrate using an automatic amino acid analyzer (L-8500 Amino Acid Analyzer, manufactured by Hitachi Co. Ltd.) to quantify the amount of collagen contained in the concentrate. In addition, by following Galambos method, the amount of uronic acid was determined to calculate the amount of proteoglycan. Still furthermore, by using high speed liquid chromatography (TSK-GEL G4000PWXL column, manufactured by Shimadzu Corporation), the molecular weight of proteoglycan was determined.

As a result of these analyses, it was found that the solid includes 43.5% of protein, 19.5% of ash contents, 37.0% of carbohydrates and 0.0% of lipids. According to the description of Patent Document 1, the weight ratio of the core protein in proteoglycan is about 7.0%. Thus, the presumed purity of the proteoglycan of the present invention was calculated to be 49.2% (i.e., (carbohydrates×0.07+lipids)/(carbohydrates+proteins+lipids)×100=49.2%). In addition, it was found that the molecular weight of proteoglycan is about 1,700,000 Dalton.

Example 6

Cartilage which had been manually removed from a shark was chopped using an electric meat chopper into, tiny pieces in minced shape and immersed in acetone, and the cartilage was dehydrated and defatted. 12.00 g of the treated cartilage, after air drying or drying under reduced pressure, were used as a starting material. To a 5 liter extraction vessel, 1678.74 g of distilled water that had been previously chilled to 5° C. was added and 1.26 g of solid sodium hydroxide was further added thereto to prepare 1680.00 g in total of an aqueous solution of sodium hydroxide (0.02 N). To this extraction vessel, the above-described starting material (12.00 g) was added and immersed for 9 hours while stirring the contents with a stirrer.

Upon completion of the immersion, the contents were transferred to another vessel over which a stainless steel filter (1 mm) was placed so that the cartilage is removed and an extract including proteoglycan can be recovered.

The extract was subjected to centrifugation for 20 minutes at 3000 rpm by using a centrifuge (Hitachi himacCF7D2 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using BIOMAX 100K POLYETHERSULFONE (cut-off molecular weight 100,000 Dalton, manufactured by Millipore, Japan), cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 12.00 g of the staring material, 1.36 g of dried solid, which corresponds to 11.36% of the starting material in a conversion value, was obtained.

Furthermore, the amount of amino acid was determined by testing the concentrate using an automatic amino acid analyzer (L-8500 Amino Acid Analyzer, manufactured by Hitachi Co. Ltd.) to quantify the amount of collagen contained in the concentrate. In addition, by following Galambos method, the amount of uronic acid was determined to calculate the amount of proteoglycan. Still furthermore, by using high speed liquid chromatography (TSK-GEL G4000PWXL column, manufactured by Shimadzu Corporation), the molecular weight of proteoglycan was determined.

As a result of these analyses, it was found that the solid includes 37.8% of protein, 27.4% of ash contents, 37.8% of carbohydrates and 0.0% of lipids. According to the description of Patent Document 1, the weight ratio of the core protein in proteoglycan is about 7.0%. Thus, the presumed purity of the proteoglycan of the present invention was calculated to be 55.7% (i.e., (carbohydrates×0.07+lipids)/(carbohydrates+proteins+lipids)×100=55.7%). In addition, it was found that the molecular weight of proteoglycan is about 1,500,000 Dalton.

Example 7

Outer skin of a squid was manually peeled off and immersed in acetone, and it was dehydrated and defatted. The treated outer skin, after air drying or drying under reduced pressure, were used as a starting material. After cutting the skin into fine pieces with scissors and then grinding them using a mortar, a dried outer skin of a squid was prepared. To a 10 liter extraction vessel, 5036.20 g of distilled water that had been previously chilled to 5° C. was added and 3.80 g of solid sodium hydroxide was further added thereto to prepare 5040 g in total of an aqueous solution of sodium hydroxide (0.02 N). To this extraction vessel, the above-described dried outer skin (33.70 g) was added and immersed for 9 hours while stirring the contents with a stirrer.

Upon completion of the immersion, the contents were transferred to another vessel over which a stainless steel filter (1 mm) was placed so that the outer skin is removed and an extract including proteoglycan can be recovered.

The extract was subjected to centrifugation for 20 minutes at 3000 rpm by using a centrifuge (Hitachi himacCF7D2 type). As a result, solids and oily portions were removed and a liquid phase including proteoglycan was recovered.

Then, the liquid phase was filtered through a filter paper (manufactured by Advantec) followed by addition of distilled water with a volume six times more than that of the filtrate. Subsequently, by using BIOMAX 100K POLYETHERSULFONE (cut-off molecular weight 100,000 Dalton, manufactured by Millipore, Japan) cut-off and concentration were carried out at the same time.

A fraction of thus obtained concentrate was taken and used for determining the solid weight in the liquid. With a drying furnace (YAMATO DX401), the concentrate fraction was dried at 105° C. for 16 hours to completely evaporate moisture. Fine measurement of the remaining solid was carried out by using a digital weighing machine (GF-400 manufactured by A&D Corp.). As a result, it was found that from 33.70 g of the dried outer skin, 16.10 g of dried solid, which corresponds to 47.7% of the starting material in a conversion value, was obtained.

Furthermore, the amount of amino acid was determined by testing the concentrate using an automatic amino acid analyzer (L-8500 Amino Acid Analyzer, manufactured by Hitachi Co. Ltd.) to quantify the amount of collagen contained in the concentrate. In addition, by following Galambos method, the amount of uronic acid was determined to calculate the amount of proteoglycan. Still furthermore, by using high speed liquid chromatography (TSK-GEL G4000PWXL column, manufactured by Shimadzu Corporation), the molecular weight of proteoglycan was determined.

As a result of these analyses, it was found that the solid includes 91.7% of protein, 1.9% of ash contents, 6.4% of carbohydrates and 0.0% of lipids. According to the description of Patent Document 1, the weight ratio of the core protein in proteoglycan is about 7.0%. Thus, the presumed purity of the proteoglycan of the present invention was calculated to be 7.0% (i.e., (carbohydrates×0.07+lipids)/(carbohydrates+proteins+lipids)×100=7.0%). In addition, it was found that the molecular weight of proteoglycan is about 1,700,000 Dalton.

The invention claimed is:

1. A process for producing proteoglycan comprising:
   (1) immersing a biological sample in an alkali solution of 0.0025 N to 0.05 N at 0° C. to 10° C., wherein said biological sample contains proteoglycan which is present in a complex form with a protein and chondroitin or chondroitin sulfate chains;
   (2) removing residuals from the alkali solution upon the termination of the immersion;
   (3) recovering an alkali solution as an extract, wherein said extract includes the proteoglycan;
   (4) filtering the extract; and
   (5) ultrafiltering through an ultrafilter membrane, thereby achieving a desired cut-off molecular weight and a desired concentration at the same time.

2. The process for producing proteoglycan according to claim 1 wherein the alkali solution is a solution of alkali metal salt.

3. The process for producing proteoglycan according to claim 1 wherein the biological sample containing proteoglycan is a cartilage tissue, muscular fibrils or leather of a fish, a mollusk, a bird or a mammal.

4. The process for producing proteoglycan according to claim 3 wherein the biological sample containing proteoglycan is a cartilage tissue of a fish, a bird or a mammal.

5. The process for producing proteoglycan according to claim 1, wherein the cut-off molecular weight is 100,000 Dalton.

6. The process for producing proteoglycan according to claim 1, wherein the biological sample containing proteoglycan is defatted.

* * * * *